US009012153B2

(12) United States Patent
Kumihashi et al.

(10) Patent No.: US 9,012,153 B2
(45) Date of Patent: Apr. 21, 2015

(54) METHOD FOR SCREENING OLFACTORY SENSIBILITY INHIBITOR

(75) Inventors: Kentaro Kumihashi, Haga-gun (JP); Hirohiko Ishida, Sumida-ku (JP); Takashi Kurahashi, Osaka (JP)

(73) Assignee: Kao Corporation, Tokyo (JP)

( * ) Notice: Subject to any disclaimer, the term of this patent is extended or adjusted under 35 U.S.C. 154(b) by 600 days.

(21) Appl. No.: 12/936,978

(22) PCT Filed: Apr. 10, 2009

(86) PCT No.: PCT/JP2009/001677
§ 371 (c)(1),
(2), (4) Date: Oct. 8, 2010

(87) PCT Pub. No.: WO2009/125604
PCT Pub. Date: Oct. 15, 2009

(65) Prior Publication Data
US 2011/0050246 A1   Mar. 3, 2011

(30) Foreign Application Priority Data

Apr. 11, 2008  (JP) ................................. 2008-103750

(51) Int. Cl.
*G01N 33/53*   (2006.01)
*G01N 33/68*   (2006.01)
*G01N 33/566*  (2006.01)

(52) U.S. Cl.
CPC .......... *G01N 33/6872* (2013.01); *G01N 33/566* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,525,329 | A | 6/1996 | Snyder et al. |
| 7,138,107 | B2 | 11/2006 | Adams et al. |
| 2003/0170608 | A1 | 9/2003 | Pronin et al. |
| 2006/0057640 | A1 | 3/2006 | Matsunami et al. |
| 2008/0009015 | A1 | 1/2008 | Hung et al. |

FOREIGN PATENT DOCUMENTS

| | | |
|---|---|---|
| CN | 1610830 A | 4/2005 |
| CN | 1882689 A | 12/2006 |
| JP | 2000-154396 | 6/2000 |
| JP | 2001-128695 | 5/2001 |
| JP | 2005-053887 | 3/2005 |
| JP | 2005-508149 | 3/2005 |
| JP | 2008-503201 | 2/2008 |
| JP | 2008-503220 | 2/2008 |
| WO | WO 03/004611 A2 | 1/2003 |
| WO | WO 03/006482 A2 | 1/2003 |
| WO | WO 2005/051984 A2 | 6/2005 |

OTHER PUBLICATIONS

International Search Report for PCT/JP2009/001677, mailed Jul. 29, 2009 , the Japanese Patent Office, Tokyo, Japan.
International Preliminary Report on Patentability (Chapter I) and Written Opinion for PCT/JP2009/001677, issued Nov. 30, 2010, The International Bureau of WIPO, Geneva, Switzerland.
Araneda, RC et al., "The molecular receptive range of an odorant receptor," Nature Neurosci 3(12): 1248-1255 (Dec. 2000), Nature Publishing Group, United States.
Belluscio, L et al., "Mice deficient in $G_{olf}$ are anosmic," Neuron 20(1): 69-81 (Jan. 1998), Cell Press, United States.
Brunet, LJ et al., "General anosmia caused by a targeted disruption of the mouse olfactory cyclic nucleotide-gated cation channel," Neuron 17(4): 681-693 (Oct. 1996), Cell Press, United States.
Delgado, R et al., "Presence of $Ca^{2+}$-Dependent $K^+$ Channels in Chemosensory Cilia Support a Role in Odor Transduction," J Neurophysiol 90: 2022-2028 (Sep. 2003), American Physiological Society, United States.
Kawai, F et al., "Nonselective Suppression of Voltage-gated Currents by Odorants in the Newt Olfactory Receptor Cells," J Gen Physiol 109: 265-272 (Feb. 1997), Rockefeller University Press, United States.
Kurahashi, T., "Olfactory Signal Transduction: Main Stream and Modulation," ("Kyusaibo ni Okeru Joho Henkan Kiko to Modulation"), Biological Physics (Seibutsu Butsuri) 40: 38-43 (2000), The Biophysical Society of Japan, Japan.
Wong, ST, "Disruption of the type III adenylyl cyclase gene leads to peripheral and behavioral anosmia in transgenic mice," Neuron 27(3): 487-497 (Sep. 2000), Cell Press, United States.
Yoshigi, H., "About deodorization and masking," Fragrance Journal (Fureguransu Janaru) 2:12-17 (1974), Fureguransujanaru Co. Inc., Japan.
Extended European Search Report for EP Patent Application No. 09730226.9, mailed Sep. 5, 2011, the European Patent Office, Munich, Germany.

(Continued)

*Primary Examiner* — Michael Pak
(74) *Attorney, Agent, or Firm* — Sterne, Kessler, Goldstein & Fox P.L.L.C.

(57) ABSTRACT

To provide a method for objectively evaluating or screening to identify a substance which is capable of suppressing or regulating olfaction. A method of evaluating or screening to identify an agent for suppressing olfactory sensitivity, including adding a test substance to a substrate having a voltage-dependent cation channel and evaluating or selecting a substance that inhibits an electrical activity caused by the cation channel. A method of evaluating or screening to identify an agent for suppressing olfactory sensitivity, including the following steps (1) to (4): (1) adding a test substance to a substrate having a voltage-dependent cation channel; (2) measuring electrical activity caused by the voltage-dependent cation channel; (3) comparing the electrical activity measured in step (2) with the corresponding electrical activity in a control group; and (4) evaluating or selecting the test substance that inhibits the electrical activity as an agent for suppressing olfactory sensitivity, based on the results obtained in step (3).

18 Claims, 2 Drawing Sheets

(56) References Cited

OTHER PUBLICATIONS

Hegg, C.C. et al., "Dopamine Reduces Odor- and Elevated-K+-Induced Calcium Responses in Mouse Olfactory Receptor Neurons In Situ," J Neurophysiol, Apr. 2004; 91: 1492-1499, American Physiological Society, Bethesda, MD.

Takeuchi, H. et al., "Mechanism of olfactory masking in the sensory cillia," J. Gen. Physiol., Jun. 2009; 133: 583-601, Rockefeller University Press, New York, NY.

Notification of the First Office Action, Chinese Patent Application No. 200980108210.X, mailed Nov. 14, 2012, Patent Office of the People's Republic of China, Beijing, China.

Vargas G et al., "Modulation by PKA of the hyperpolarization-activated current ($I_h$) in cultured rat olfactory receptor neurons," J Membr Biol, Jul. 2002; 188(2): 115-125, Springer, New York.

METHOD FOR SCREENING OLFACTORY SENSIBILITY INHIBITOR

FIELD OF THE INVENTION

The present invention relates to a method of evaluating an agent for suppressing olfactory sensitivity or a screening method to identify the same employing a voltage-dependent cation channel.

BACKGROUND OF THE INVENTION

Perception of odor begins at the olfactory receptor cells present in the olfactory mucosa with receiving odorant molecules suspended in the air by their olfactory receptors. The olfactory receptors, which are a G-protein-coupled receptor, are activated when bound to an odorant molecule and produce cAMP by the mediation of G-protein and adenylate cyclase. Then, cyclic nucleotide-gated (CNG) channel on the olfactory receptor cells are activated by cAMP, and ions influx through the activated channel, whereby the olfactory receptor cells is depolarized. As a result, voltage-dependent channels are opened, and action potentials are generated, to thereby transfer odor-related information to the central nervous system.

Masking of olfaction is accomplished by temporarily inactivating or lessening the aforementioned response and is thought to be more effectively attained when combined with information processing in the central nervous system such as lateral inhibition. Masking of olfaction by fragrance is supposed to affect the affinity of an odor substance to the olfactory mucosa. Some fragrance substances are suggested to have an anesthetic action based on inhibition of enzymatic activity in the olfactory receptor cells (Non-Patent Document 1). However, there has been reported no technique for verifying or objectively evaluating the aforementioned action. Hitherto, such an action must be evaluated through a subjective sensory test in the development of potent olfaction-masking agents.

It is indicated that olfaction is inhibited by inhibiting the information transfer system in the olfactory receptor cells. Actually, some tests employing knockout mice have revealed that olfaction is nullified by lack of signaling molecules: olfactory cell G-protein (Golf) (Non-Patent Document 2), type-III adenylate cyclase (Non-Patent Document 3), and olfactory CNG channel subunit (Non-Patent Document 4). As the olfactory CNG channel is exposed to the olfactory cilia membrane the activity of the CNG channel can be regulated without penetration of an activity-regulating substance through the cell membrane or epithelial cell barrier. Thus, the olfactory CNG channel is an important target to regulate olfaction (Patent Document 1). For example, it has been disclosed that inhibition of the CNG channel by a calcium channel inhibitor reduces olfaction of rats (Patent Document 2). There have been proposed other mechanisms which can be involved in masking of olfaction in the olfactory mucosa, such as a theoretical mechanism employing an antagonist against the olfactory receptor (Non-Patent Document 5) and a theoretical mechanism employing a calcium-dependent potassium channel (Non-Patent Document 6). There have been proposed methods for modulating olfactory sensitivity by inhibition of cAMP-decomposing enzyme in the olfactory cilia (Patent Document 3), controlling the intracellular calcium level (Patent Document 4), and employing an odor-ingredient compound analogue (Patent Document 5).

The voltage-dependent cation channels present on the olfactory receptor cells generate action potential through depolarization of the olfactory receptor cells caused by the CNG channel activity and thus are involved in olfaction transfer. A study has revealed that some odorant molecules inhibit the voltage-dependent cation channels in isolated olfactory receptor cells (Non-Patent Document 7). However, in vivo, most of the voltage-dependent cation channels are present on the cell membranes protected by tight junctions and are not exposed to the olfactory cilia membrane, unlike with the CNG channels. Although various mechanisms as those described above are known to relate to the masking of olfaction, it has not been clearly elucidated whether the voltage-dependent cation channel is involved in olfactory masking.

PRIOR ART DOCUMENTS

Patent Documents

Patent Document 1: Japanese Kohyo (PCT) Patent Publication No. 2005-500836
Patent Document 2: U.S. Pat. No. 7,138,107
Patent Document 3: U.S. Pat. No. 5,525,329
Patent Document 4: Japanese Patent Application Laid-Open (kokai) No. 2000-154396
Patent Document 5: Japanese Patent Application Laid-Open (kokai) No. 2005-53887

Non-Patent Documents

Non-Patent Document 1: Hideki Yoshigi, Fragrance Journal (1974) Vol. 2, No. 3, 12-17
Non-Patent Document 2: Belluscio et al., Neuron (1998), vol. 20: 69-81
Non-Patent Document 3: Wong et al., Neuron (2000), vol. 27: 487-497
Non-Patent Document 4: Brunet et al., Neuron (1996), vol. 17: 681-693
Non-Patent Document 5: Araneda et al., Nat. Neurosci. (2000), vol. 3: 1248-1255
Non-Patent Document 6: Delgado et al., J. Neurophysiol. (2003), vol. 90: 2022-2028
Non-Patent Document 7: Kawai et al., J. Gen. Physiol. (1997), vol. 109: 265-272

SUMMARY OF THE INVENTION

The present invention provides the following:

(I) a method of evaluating or screening to identify an agent for suppressing olfactory sensitivity, comprising adding a test substance to a substrate having a voltage-dependent cation channel and evaluating or selecting a substance that inhibits an electrical activity caused by the cation channel.

(II) a method of evaluating or screening to identify an agent for suppressing olfactory sensitivity, comprising the following steps (1) to (4):

(1) adding a test substance to a substrate having a voltage-dependent cation channel;
(2) measuring electrical activity caused by the voltage-dependent cation channel;
(3) comparing the electrical activity measured in step (2) with the corresponding electrical activity in a control group; and
(4) evaluating or selecting the test substance that inhibits the electrical activity as an agent for suppressing olfactory sensitivity, based on the results obtained in step (3).

(III) a method according to (I), wherein the voltage-dependent cation channel is a voltage-dependent cation channel derived from an olfactory receptor cell.

DETAILED DESCRIPTION OF THE INVENTION

Figure 1:
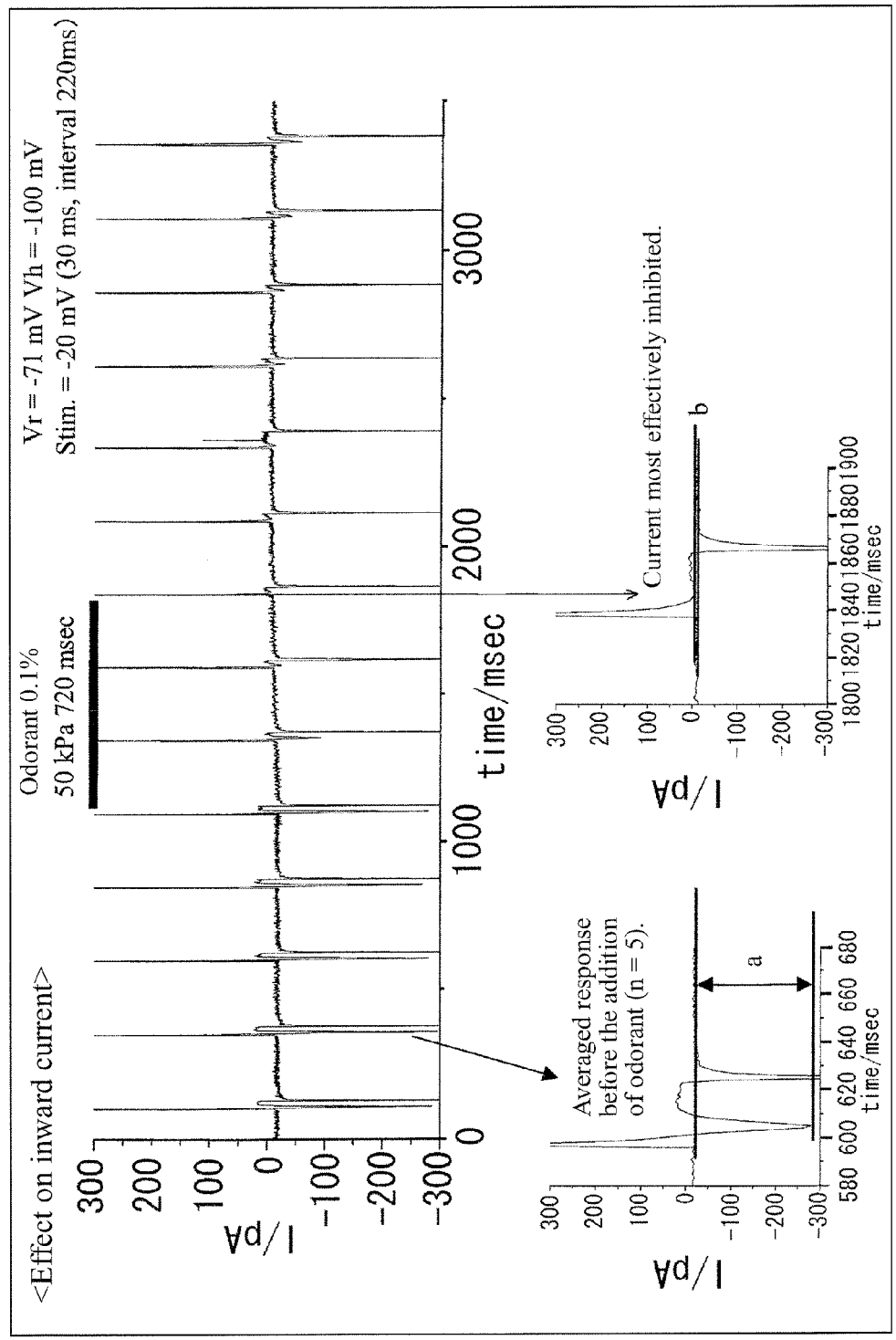
FIG. 1 Measurement of inhibitory effect of a test substance on the activity of a voltage-dependent cation channel.

The present invention is directed to providing a method for objectively evaluating or selecting to identify a substance which is capable of suppressing or regulating olfaction.

The present inventors have carried out studies on a method for objectively evaluating or selecting to identify a substance that can suppress or regulate olfaction, and have found that a correlation exists between the inhibitory effect of a given compound on voltage-dependent cation channels in the olfactory receptor cell and the odor-suppressing efficacy of the compound evaluated by a subjective sensory method. The present invention has been accomplished on the basis of this finding.

According to the method of the present invention, a substance that suppresses olfactory sensitivity, which has conventionally been evaluated by a subjective sensory test, is evaluated or identified by screening objectively and effectively.

Hereinafter, the screening method of the present invention will be described in detail.

In the method of evaluating or screening to identify an agent for suppressing olfactory sensitivity of the present invention, a substrate having a voltage-dependent cation channel is employed, and a test substance, which is a candidate of the agent for suppressing olfactory sensitivity, is added to the substrate. The test substance that inhibits the electrical activity generated by the cation channel is evaluated or selected as an agent for suppressing olfactory sensitivity. As shown in the Examples described hereinbelow, the effect of a test substance on the electrical activity generated by voltage-dependent cation channels present in the olfactory receptor cells of *Cynops pyrrhogaster* was evaluated, while the olfaction-masking effect of the test substance was also evaluated by a sensory test. As a result, a substance which exhibits higher voltage-dependent cation channel-inhibitory effect has been found to attain higher olfaction-masking effect. Accordingly, the substance that inhibits the electrical activity generated by a voltage-dependent cation channel is a useful as an agent for suppressing olfactory sensitivity, and an agent for suppressing olfactory sensitivity is evaluated or identified by screening based on the percent inhibition of voltage-dependent cation channel as an index.

The "substrate having a voltage-dependent cation channel" includes biomaterials having a voltage-dependent cation channel. Examples of the biomaterials having a voltage-dependent cation channel include olfactory receptor(s) or olfactory cell(s) which is/are isolated from biological bodies and cultured products thereof; an olfactory cell membrane bearing a voltage-dependent cation channel; recombinant cell(s) genetically modified so as to express a voltage-dependent cation channel and cultured products thereof; a membrane of the recombinant cells; and an artificial lipid bilayer membrane having a voltage-dependent cation channel.

Examples of the "voltage-dependent cation channel" include cation channels derived from biological cells or from cultured products of the cells; those derived from recombinant cells genetically modified so as to express a voltage-dependent cation channel; and those synthesized ex vivo. No particular limitation is imposed on the type of the voltage-dependent cation channel, and voltage-dependent $Na^+$-channel, voltage-dependent $K^+$-channel, and voltage-dependent $Ca^{2+}$-channel (including L-Type, N-Type, P-Type, Q-Type, R-Type, and T-Type) may be employed. So long as the functions of the voltage-dependent cation channel are maintained, the cation channel may be a fragment of the channel or a recombinant product thereof. The voltage-dependent cation channel is preferably derived from olfactory receptor cells.

The "electrical activity caused by a voltage-dependent cation channel" measured in the present invention may be any electrical activity which is generally measured in the art and are caused by the voltage-dependent cation channel. More specifically, the electrical activity may be a change in current or voltage caused by opening the channel. Examples of the electrical activity include the peak amplitude, width, or area of membrane depolarization potential or action potential; the number or frequency of action potential spikes; the peak amplitude, width, or area of inward current flowing through the channel; and the period of time required for restoring the changed value of any of the above parameters after administration of a test substance to the level before administration. The electrical activity may be measured as a single channel activity or an activity of a group of channels.

More specifically, the method of the present invention is carried out by the following steps:

(1) adding a test substance to a substrate having a voltage-dependent cation channel;

(2) measuring electrical activity caused by the voltage-dependent cation channel;

(3) comparing the electrical activity measured in step (2) with the corresponding electrical activity in a control group; and (4) evaluating or selecting the test substance that inhibits the electrical activity as an agent for suppressing olfactory sensitivity, based on the results obtained in step (3).

In the above steps, the substrate having a voltage-dependent cation channel is maintained under the conditions where the channel maintains its activity and has a potential for eliciting electrical activity. The maintenance conditions vary depending on the type of the substrate used, the way of measuring the electrical activity, etc. However, those skilled in the art may appropriately select the conditions accordingly.

In step (1), the test substance is added to a voltage-dependent cation channel such that the test substance is placed close to or brought into contact with the channel so as to attain the potential inhibitory effect thereof. The methodology of adding the test substance varies depending on the type of the substrate used, the way of measuring the electrical activity, etc. However, those skilled in the art may appropriately select the methodology accordingly. For example, the test substance may be added to a liquid in which the substrate is immersed. Alternatively, a solution of the test substance may be sprayed through a pipette or the like placed in the vicinity of the substrate.

In the measurement of electrical activity in step (2), any electrical activity caused by a voltage-dependent cation channel as described above may be measured through a commonly-used method. Examples of the method for the measurement include patch-clamp methods such as the outside-out method, the inside-out method, the perforated patch method, or the whole-cell recording method. Of these, the whole-cell recording method is preferred. The patch-clamp methods may be conducted by established high-throughput assays (e.g., IonWorks Quattro). Thus, the method of the present invention may be conducted using these high-throughput assays. Electrical activity by a voltage-dependent cation channel may be induced by: temporarily depolarizing cell membrane while the membrane potential is fixed; temporarily loading electric current to cells in a constant current mode; or adding a solution or agent that depolarizes cells (e.g., KCl solution) to the outside of the cells. The procedure of the patch-clamp method is described in detail in, for example, "New Patch-Clamp Experimental Techniques" (edited by Yasunobu OKADA, Yoshioka-Shoten, 2001).

Alternatively, the fluorescence or emission attributed to electrical activity may be measured, or the image measurement method may be employed. In an exemplified procedure, a substrate or cells to which a membrane-potential-sensitive dye has been applied in advance are brought into contact with a test substance. The fluorescence of test cells in the presence of the test substance is monitored, and the results are compared with those obtained in the absence of the test substance, whereby the degree of inhibition of the voltage-dependent cation channel can be determined. In the present method, physical properties such as fluorescence may be monitored by means of a fluorometric imaging plate reader (FRIPR) or a voltage/ion probe plate reader (VIPR). Examples of the fluorescence dye which may be employed in the test include a calcium-sensitive dye and a fluorescence sodium dye.

The electrical activity measured according to the method of the present invention is compared with the electrical activity obtained by the control group. Examples of the "comparison with the control group" include: comparison of the electrical activity before administration of the test substance with that after administration of the test substance; comparison of the electrical activity before removal of the test substance with that after removal of the test substance; and comparison of the electrical activity of the control-substance-added group with that of the group to which no control substance has been added.

Based on the results obtained through the steps, the test substance that exhibits an inhibitory effect on a voltage-dependent cation channel may be evaluated or selected as an agent for suppressing olfactory sensitivity. As shown in the Examples hereinbelow, a substance that exhibits higher inhibitory effect on electrical activity of a voltage-dependent cation channel exhibits higher olfaction masking effect in a sensory test. Therefore, a substance that exhibits higher inhibitory effect on electrical activity of a voltage-dependent cation channel may be evaluated or selected as an agent that suppresses olfactory sensitivity more effectively.

EXAMPLES

The present invention will next be described in more detail by way of Examples.

Example 1

1. Isolation of Olfactory Receptor Cells

Olfactory receptor cells were isolated from newts (*Cynops pyrrhogaster*) through a known method (Kurahashi et al., J. Physiol. (1989), 419: 177-192) and bathed in a normal Ringer's solution. More specifically, each newt which had been hibernated in ice-water was double-pithed, and the skull thereof was cut, to thereby remove the olfactory membrane. The removed olfactory membrane was incubated in 0.1% collagenase solution at 37° C. for five minutes. After washing off collagenase, the membrane tissue was broken by means of a glass pipette, to thereby isolate olfactory cells. The normal Ringer's solution had the following composition: NaCl 110 mM, KCl 3.7 mM, $CaCl_2$ 3 mM, $MgCl_2$ 1 mM, glucose 15 mM, sodium pyruvate 1 mM, HEPES 2 mM, and Phenol Red 0.001% (w/v), with a pH of 7.4 (adjusted with NaOH).

2. Measurement of Electrical Activity

A. Conditions

The membrane current of the isolated olfactory cells was recorded through the whole-cell recording method, while the membrane potential was fixed (Kawai et al., J. Gen. Physiol. (1997), vol. 109: 265-272). The electrode employed was produced from borosilicate glass capillary (diameter: 1.2 mm) by means of a puller for electrode fabrication (PP-830, product of Narishige Scientific Instruments). The electrode had a resistance of 10 to 30 MΩ. Then, an electrode solution was added in the electrode, and an Ag—AgCl wire was inserted into the electrode. The Ag—AgCl wire was connected to a patch-clamp amplifier (Axopatch 1D, 200B, product of Axon Instrument), whereby fixation of the membrane potential and depolarization stimulation were performed. The employed electrode solution had the following composition: KCl 120 mM, HEPES 2 mM, and Phenol Red 0.001% (w/v), with a pH of 7.4 (adjusted with KOH). The membrane current was recorded by a computer which was connected by the mediation of the patch-clamp amplifier and an A/D converter (Digidata 1320, product of Axon Instrument). Each test substance was sprayed to the cells for stimulation, by means of a pressure-controller. The pressure controller is an apparatus which reduces the pressure of compressed air supplied by means of an air-compressor to a specific value under computer-controlled conditions and which feeds the compressed air for a predetermined period of time to a tail of the glass pipette in which the test substance has been charged (Ito et al., The Japanese Journal of Physiology, 1995, vol. 57, 127-133).

B. Procedure

In order to investigate the effect of the test substance on the voltage-dependent cation channel activity, the membrane potential of the isolated olfactory cells was fixed to −100 mV, and depolarized to −20 mV for 20 ms at intervals of 200 ms. The peak amplitude of the inward current elicited immediately after depolarization was measured. Each of the test substances shown in Table 1 (1 μL) was mixed with the normal Ringer's solution (1 mL). Under continuous depolarization stimulation, the mixture was sprayed toward the olfactory cells (720 ms, at 50 kPa) through a glass pipette (tip diameter: 1 μm) that was placed such that the tip of the pipette was located in the vicinity (≤20%) of the olfactory cells to add the mixture to the olfactory cells, and the change in inward current was monitored. Stimulation of one olfactory cell by the test substance was performed three times, and the three inward currents obtained from the cell were averaged. Each test substance was tested by three olfactory cells, and the three inward currents obtained from the cells were averaged. During the test, in very rare cases, the olfactory receptor responded to stimulation by the test substance, and inward current attributed to a CNG channel was observed. However, such cases were eliminated for evaluation. One conceivable reason for occurrence of such a case is that the test substance acts as an antagonist to the olfactory receptor on the olfactory cell employed in the test. CNG channel current is readily distinguishable from voltage-dependent channel current in terms of amplitude, peak shape, and duration. FIG. 1 shows exemplary current data obtained in the test.

C. Results

The average change in inward current caused by addition of a test substance (b; see FIG. 1) was compared with the average peak amplitude of inward current caused by 5-times depolarization before addition of the test substance (a; see FIG. 1) (control), whereby the inhibitory effect of the test substance on electrical activity of the voltage-dependent cation channel was evaluated by the percent inward current inhibition represented by the following formula:

Percent inward current inhibition=$(1-b/a)\times100$(%).

Table 1 also shows the percent inward current inhibition values of the test substances. Some test substances completely inhibited generation of inward current concomitant with depolarization of olfactory cells.

TABLE 1

| Perfumes (Test substances) | Percent inward current inhibition (%) |
|---|---|
| Benzyl acetate | 110.8 |
| Citral | 110.6 |
| Dihydromyrcenol | 109.0 |
| n-Nonanal | 107.4 |
| Methyl dihydrojasmonate | 107.1 |
| Linalool | 106.5 |
| 2-Methyl-4-(2,2,3-trimethyl-3-cyclopenten-1-yl)-2-buten-1-ol (Sandalmysore Core, Trademark, Kao Corporation) | 105.6 |
| Eugenol | 105.0 |
| Benzaldehyde | 95.4 |
| Isoamyl acetate | 92.0 |
| Geraniol | 90.1 |
| Anisaldehyde | 89.3 |
| β-Phenylethyl alcohol | 82.6 |
| 2,4-Dimethyl-3-cyclohexene-1-carboxaldehyde (Triplal, Trademark, IFF) | 79.9 |
| cis-3-Hexenol | 78.7 |
| p-tert-Butyl-α-methylhydrocinnamaldehyde (Lysmeral, Trademark, BASF) | 57.9 |
| β-Damascone | 56.1 |
| Ethyl 2-cyclohexylpropionate (Poirenate, Trademark, Kao Corporation) | 48.7 |
| 1,8-Cineole | 46.5 |
| Linalyl acetate | 43.3 |
| Ethyl 2-methylbutyrate | 42.0 |
| 4-(4-Hydroxy-4-methylpentyl)-3-cyclohexene-1-carboxaldehyde (Lyral, Trademark, IFF) | 35.7 |
| 1-(2-tert-Butylcyclohexyloxy)-2-butanol (Amber Core, Trademark, Kao Corporation) | 27.1 |
| o-tert-Butylcyclohexyl acetate | 23.8 |
| Ethyltricyclo[5.2.1.0$^{2,6}$]decane-2-carboxylate (Fruitate, Trademark, Kao Corporation) | 11.6 |
| Benzyl benzoate | 10.7 |

Example 2

A. Procedure

An olfactory masking test based on sensory evaluation was performed with 20 specialists. Isovaleric acid (1%) was used as a malodorous substance, and each of the substances listed in Table 2 was employed as a masking material. The malodorous substance (2 μL) and each test substance (4 μl) were separately absorbed by cotton balls (diameter: 1 cm), and placed in each injection syringe (capacity: 50 mL) at room temperature for 12 hours to vaporized the substance therein. Both the vaporized malodorous substance and the vaporized test substance were injected into a PP bottle (capacity: 500 mL) with a cap and admixed in the bottle. In evaluation, each specialist slightly opened the cap of the PP bottle and smelled the odor in the bottle, whereby the masking score was determined. The masking score was evaluated by the following six criteria, based on the intensity of odor in a PP bottle to which only the malodorous substance had been added.

0: No masking effect
1: Only slight masking effect
2: Some masking effect
3: Satisfactory masking effect
4: Substantially complete masking effect
5: Complete masking effect

TABLE 2

| Perfumes (Test substances) |
|---|
| Dihydromyrcenol |
| 4-(4-Hydroxy-4-methylpentyl)-3-cyclohexene-1-carboxaldehyde (Lyral, Trademark, IFF) |
| Ethyl 2-cyclohexylpropionate (Poirenate, Trademark, Kao Corporation) |
| 1-(2-tert-Butylcyclohexyloxy)-2-butanol (Amber Core, Trademark, Kao Corporation) |
| o-tert-Butylcyclohexyl acetate |
| β-Damascone |
| β-Phenylethyl alcohol |
| isoamyl acetate |
| 2,4-Dimethyl-3-cyclohexene-1-carboxaldehyde (Triplal, Trademark, IFF) |
| Citral |
| Ethyltricyclo[5.2.1.0$^{2,6}$]decane-2-carboxylate (Fruitate, Trademark, Kao Corporation) |
| Benzaldehyde |
| cis-3-Hexenol |
| 1,8-Cineole |
| Linalool |
| Benzyl benzoate |
| p-tert-Butyl-α-methylhydrocinnamaldehyde (Lysmeral, Trademark, BASF) |
| Anisaldehyde |
| Linalyl acetate |
| Geraniol |

B. Results

Figure 2:
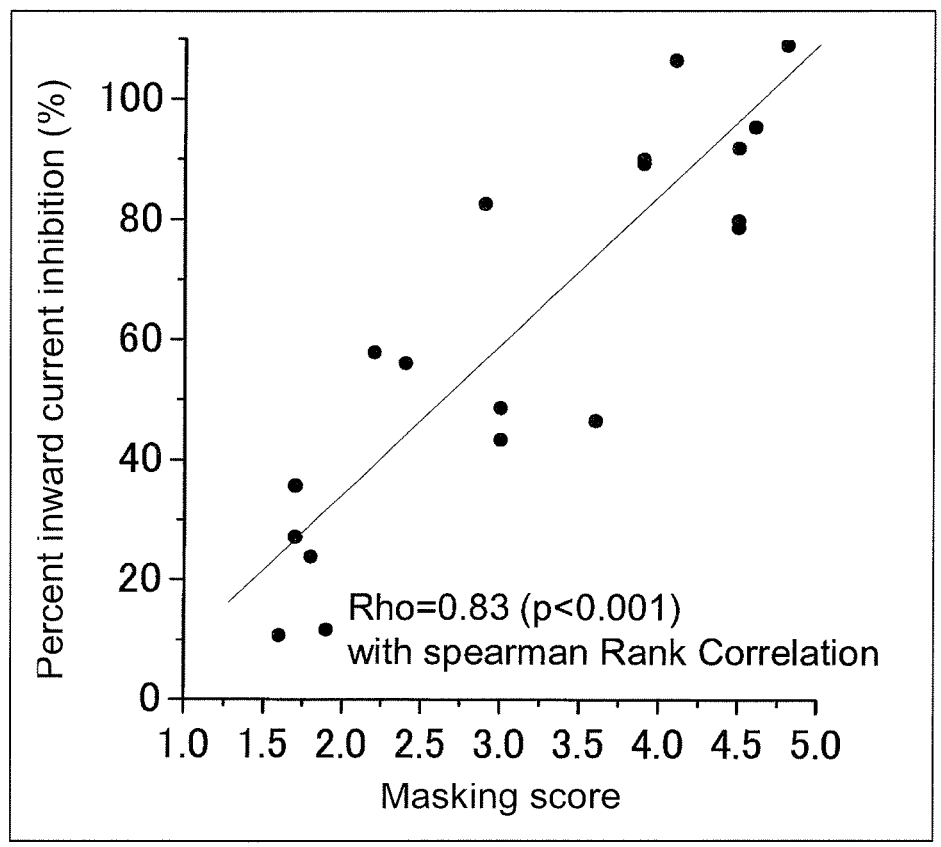
FIG. 2 The relationship between the inhibitory effects on voltage-dependent cation channels and olfaction masking effects.

Table 3 shows the sensory test results. The tested substances exhibited a wide range of masking scores. Table 3 also shows the percent inward current inhibition values of the tested substances which were calculated in the experiments of Example 1. As is clear from Table 3, a substance exhibiting higher inhibitory effect on voltage-dependent cation channel activity was found to exhibit intense masking effect. As shown in FIG. 2, percent inward current inhibition was found to be highly correlated to masking effect. Therefore, any substance exhibiting higher inhibitory effect on voltage-dependent cation channel activity was found to exhibit stronger olfactory masking effect.

TABLE 3

| Perfumes (Test substances) | Masking score | Percent inward current inhibition (%) |
|---|---|---|
| Dihydromyrcenol | 4.8 | 109.0 |
| 4-(4-Hydroxy-4-methylpentyl)-3-cyclohexene-1-carboxaldehyde (Lyral, Trademark, IFF) | 1.7 | 35.7 |
| Ethyl 2-cyclohexylpropionate (Poirenate, Trademark, Kao Corporation) | 3.0 | 48.7 |
| 1-(2-tert-Butylcyclohexyloxy)-2-butanol (Amber Core, Trademark, Kao Corporation) | 1.7 | 27.1 |
| o-tert-Butylcyclohexyl acetate | 1.8 | 23.8 |
| β-Damascone | 2.4 | 56.1 |
| β-Phenylethyl alcohol | 2.9 | 82.6 |
| isoamyl acetate | 4.5 | 92.0 |
| 2,4-Dimethyl-3-cyclohexene-1-carboxaldehyde (Triplal, Trademark, IFF) | 4.5 | 79.9 |

TABLE 3-continued

| Perfumes (Test substances) | Masking score | Percent inward current inhibition (%) |
|---|---|---|
| Citral | 3.9 | 110.6 |
| Ethyltricyclo[5.2.1.0$^{2,6}$]decane-2-carboxylate (Fruitate, Trademark, Kao Corporation) | 1.9 | 11.6 |
| Benzaldehyde | 4.6 | 95.4 |
| cis-3-Hexenol | 4.5 | 78.7 |
| 1,8-Cineole | 3.6 | 46.5 |
| Linalool | 4.1 | 106.5 |
| Benzyl benzoate | 1.6 | 10.7 |
| p-tert-Butyl-α-methylhydrocinnamaldehyde (Lysmeral, Trademark, BASF) | 2.2 | 57.9 |
| Anisaldehyde | 3.9 | 89.3 |
| Linalyl acetate | 3.0 | 43.3 |
| Geraniol | 3.9 | 90.1 |

The invention claimed is:

1. A method of evaluating or screening to identify an agent that suppresses olfactory sensitivity, comprising
   (a) adding a test substance to a substrate having a voltage-dependent cation channel and determining if the substance inhibits an electrical activity caused by the voltage-dependent cation channel,
   wherein the substrate is an isolated olfactory receptor cell, a cultured olfactory receptor cell, or an olfactory cell membrane,
   wherein the electrical activity that is inhibited is the current or voltage caused by opening the channel, and wherein the electrical activity is measured using a patch-clamp, fluorescence, emission or image measurement method,
   (b) conducting an olfactory masking test in which smell is used to evaluate whether the test substance masks the odor of a malodorous substance, and
   (c) evaluating or selecting a substance that both
      (i) inhibits the electrical activity caused by the voltage-dependent cation channel in part (a)
      and (ii) masks the odor of the malodorous substance in part (b)
   as an agent that suppresses olfactory sensitivity,
   wherein the electrical activity is not activity of the CNG channel.

2. A method of evaluating or screening to identify an agent that suppresses olfactory sensitivity, comprising the following steps (1) to (5):
   (1) adding a test substance to a substrate having a voltage-dependent cation channel;
   (2) measuring an electrical activity caused by the voltage-dependent cation channel;
   wherein the substrate is an isolated olfactory receptor cell, a cultured olfactory receptor cell, or an olfactory cell membrane,
   wherein the electrical activity that is inhibited is the current or voltage caused by opening the channel, and wherein the electrical activity is measured using a patch-clamp, fluorescence, emission or image measurement method
   (3) comparing the electrical activity measured in step (2) with the corresponding electrical activity in a control group;
   (4) conducting an olfactory masking test in which smell is used to evaluate whether the test substance masks the odor of a malodorous substance, and
   (5) based on the results obtained in steps (3) and (4), evaluating or selecting a substance that both
      (i) inhibits the electrical activity of the voltage-dependent cation channel as compared with the corresponding electrical activity in a control group in step (3) and
      (ii) masks the odor of the malodorous substance in step (4) as agent that suppresses olfactory sensitivity,
   wherein the electrical activity is not activity of the CNG channel.

3. The method according to claim 1, wherein the substrate is an isolated olfactory receptor cell.

4. The method of claim 1, wherein the substrate is a cultured olfactory receptor cell.

5. The method of claim 1, wherein the substrate is an olfactory cell membrane.

6. The method of claim 1, wherein the electrical activity is measured using a patch-clamp measurement method.

7. The method of claim 1, wherein the electrical activity is measured using a fluorescence measurement method.

8. The method of claim 1, wherein the electrical activity is measured using an emission measurement method.

9. The method of claim 1, wherein the electrical activity is measured using an image measurement method.

10. The method of claim 2, wherein the substrate is an isolated olfactory receptor cell.

11. The method of claim 2, wherein the substrate is a cultured olfactory receptor cell.

12. The method of claim 2, wherein the substrate is an olfactory cell membrane.

13. The method of claim 2, wherein the electrical activity is measured using a patch-clamp measurement method.

14. The method of claim 2, wherein the electrical activity is measured using a fluorescence measurement method.

15. The method of claim 2, wherein the electrical activity is measured using an emission measurement method.

16. The method of claim 2, wherein the electrical activity is measured using an image measurement method.

17. The method of claim 1, wherein the electrical activity caused by the voltage dependent cation-channel is inward current elicited by depolarization of the substrate with fixed membrane potential.

18. The method of claim 2, wherein the electrical activity caused by the voltage dependent cation-channel is inward current elicited by depolarization of the substrate with fixed membrane potential.

* * * * *